United States Patent [19]

Shen

[11] 4,447,301

[45] May 8, 1984

[54] SONIC RESONATOR CONTROL AND METHOD FOR DETERMINING COMPONENT CONCENTRATION IN MULTIPLE COMPONENT MOLTEN LIQUIDS

[75] Inventor: Sin-Yan Shen, Woodridge, Ill.

[73] Assignee: The United States of America as represented by the United States Department of Energy, Washington, D.C.

[21] Appl. No.: 437,783

[22] Filed: Oct. 29, 1982

[51] Int. Cl.³ .......................... C25C 3/20; C25C 3/00; G06F 15/46; G06G 7/58
[52] U.S. Cl. ..................................... 204/67; 73/61 R; 204/60; 204/245; 364/497; 436/73
[58] Field of Search ...................... 422/62, 68; 436/55, 436/73, 150, 182; 73/24, 61 R; 364/497, 499, 509; 204/60, 67, 243-247, 228, 61-66, 68-71

[56] References Cited

U.S. PATENT DOCUMENTS

| | | | |
|---|---|---|---|
| 2,280,226 | 4/1942 | Firestone | 73/627 |
| 3,346,065 | 10/1967 | Bourquard | 73/24 |
| 3,444,726 | 5/1969 | Young et al. | 73/61 R |
| 4,255,964 | 3/1981 | Morison | 73/24 |
| 4,261,197 | 4/1981 | Mansfield | 73/61 R |
| 4,287,755 | 9/1981 | Mansfield | 73/61 R |

Primary Examiner—Howard S. Williams
Assistant Examiner—T. L. Williams
Attorney, Agent, or Firm—Charles F. Lind; James W. Weinberger; Michael F. Esposito

[57] ABSTRACT

This invention teaches a control to be used in smelting aluminum by the electrolysis breakdown of alumina ($Al_2O_3$) in a molten electrolyte heated to approximately 950°–1000° C. The invention provides a sonic resonator and control that can accurately detect the resonant frequency of the resonator in the molten electrolyte. The resonator preferably is made with tubular side wall ¼ of the sonic wavelength, or is a quarter wave resonator. A wave generator inputs a signal having a range of frequencies that includes the resonant frequency, so that a peak resonant output at the resonant frequency can be detected on an oscilloscope or like detector. This instantaneous resonant frequency is then checked against an accurate data base correlating the resonant frequencies of the resonator in the electrolyte at specific alumina concentrations normally experienced throughout the electrolysis cycle. The electrolysis cycle can thus be controlled and recharged at any predetermined low alumina concentration greater than where the anode effect phase of the cycle normally might begin.

8 Claims, 7 Drawing Figures

SONIC RESONATOR CONTROL AND METHOD FOR DETERMINING COMPONENT CONCENTRATION IN MULTIPLE COMPONENT MOLTEN LIQUIDS

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

The Hall process of smelting aluminum uses electrolysis of alumina ($Al_2O_3$) in a molten bath of cryolite ($Na_3AlF_6$). The process initially starts with a powdered mixture of alumina and cryolite present in an open vessel or cell having steel walls lined with carbon, the cell being heated then by electric heaters to render the mixture molten at approximately 950°–1000° C. Carbon anodes are spaced from the carbon vessel walls (operating as the cathode) and a DC potential is applied between the anodes and the vessel walls producing the electrolysis current.

During the smelting cycle, the alumina breaks down to produce metallic aluminum (Al) which sinks in the molten electrolyte mixture to the bottom of the vessel. The normal starting concentration of the alumina in the electrolyte is ideally between 6 and 7 wt.%, and this is slowly reduced over an extended cycle usually in excess of 10–12 hours to approximately 2 wt.% or less. However, at some low level of alumina concentration (between perhaps 2.2 and 0.5 wt.% but more frequently between 2 and 1 wt.%) the alumina concentration is too low to maintain normal smelting, thereby precipitating what is known as the "anode effect".

Several adverse things happen during the anode effect. A coating of carbon tetrafluoride ($CF_4$) builds up on the anode, preventing the bath from wetting the anode, and the voltage applied across the cathode and anode increases dramatically (from 4–6 volts to perhaps 20–40 volts or higher). This consequently brings about the second adverse factor, namely that because the current is kept constant (at approximately 600–800 milliamps per $cm^2$ of anode), the power input goes up, the current efficiency drops, and the cell overheats. In overheating, the cell life is reduced, and extra chemicals in the form of fluoride (F) are consumed. The cycle is normally terminated after the anode effect phase of the cycle has already started.

To restart the cycle and remove the cycle from the anode effect, a solid crust formed over the top of the molten electrolyte in the cell is first broken and more powdered alumina is added, typically from a storage hopper mounted over the cell.

The metallic aluminum is siphoned from the bottom of the cell periodically, such as after several batches of alumina have been processed.

No reliable cycle control is known and/or commercially available that can measure alumina concentration. The corrosive and high temperature environment of the molten electrolyte makes most internal controls impractical. The most common control merely detects voltage changes between the cathode and anode, but this basically results only in an after-the-fact detection, as the anode effect has already started. The normal smelting cycle will operate in the 95–85% range of current efficiency during the major part of the cycle starting with the alumina concentrations in the 6–7 wt.% range to the low range where the anode effect begins; but thereafter in only a matter of minutes the current efficiency can drop dramatically to much less than 70 or even 50% current efficiency during the anode effect phase of the cycle. See FIG. 5 for a representative curve showing this relationship. The presently used cycle controls generally prove wanting as they lack sensitivity and fail to give advance warning.

The inaccurate control of the smelting cycle and the resulting "anode effect" that normally occurs every cycle waste tremendous amounts of energy and chemical efficiency, Several anodes generally are arranged side-by-side in a single cell perhaps 5 ft. high, 50 to 150 cells are typically connected together to form a single pot line, and perhaps 15–25 pot lines may be operating in a single commercial aluminum plant. A single cell can produce about 2,000 pounds of aluminum per day, but uses approximately 6 kilowatt-hours of electrical energy and 0.5 of a pound of carbon for every pound of aluminum produced. Considering U.S. aluminum smelting only, perhaps $6 \times 10^{10}$ kilowatt hours/year could be saved with more accurate process control by automatically rebatching the process at alumina concentration of 2.5 or 2.7 wt.%, or above where the anode effect would normally ever first start.

SUMMARY OF THE INVENTION

This invention relates to a means for and method of using a sonic resonator in a binary liquid mixture in order to detect changes in the resonant frequency brought about as a function of the relative concentration of the components in the mixture. This invention particularly teaches means including a sonic resonator located in a molten binary electrolyte of cryolite and alumina used in the Hall process of smelting aluminum, and a control to detect the sonic resonant frequency of the resonator in the electrolyte for accurately determining the alumina concentration in the electrolyte over the duration of the smelting cycle.

The sonic velocity in the molten electrolyte is uniquely related to alumina concentration of the electrolyte at the electrolysis temperatures. Thus, by knowing the sonic velocity, and/or the resonant frequency of a resonator, in the electrolyte at any time during the electrolysis cycle, one can also then know the alumina concentration of the electrolyte.

This invention provides specifically for measuring the resonant sonic frequency in the molten electrolyte and comparing it against an established data base correlating the resonant sonic frequency and the alumina concentration for determining thereby the instantaneous alumina concentration.

In point of actual hardware, a resonator is positioned in the molten electrolyte and excited by an adjustable frequency generator throughout a range of frequencies including the resonant frequency of the resonator. A detector compares and identifies the sonic signals, the signals having low energy levels at all exciting frequencies except at the resonant frequency, whereat a large energy signal would be detected. The resonator and detector control would be calibrated before use by determining the resonant frequency of the electrolyte at specific known alumina concentrations, viz., at 7%, at 6%, at 5%, etc. down to the anode effect range of the electrolysis cycle. By comparing the detected resonant frequency against this data base, the instantaneous alumina concentration of the electrolyte mixture can be determined then to an accuracy better than a tenth of a percent.

The resonator might be fabricated of titanium diboride ($TiB_2$) as a tube having one closed end and having a transducer secured to the closed end; the transducer in turn might be formed of lithium niobate ($LiNbO_3$) or strontium pyroniobate ($Sr_2Nb_2O_7$).

This invention thereby can be specifically used to control the cycle time of the Hall process of smelting aluminum, and particularly signal when to add alumina to the electrolyte before the concentration thereof becomes too low and the anode effect phase of the electrolysis begins.

DETAILED DESCRIPTION OF THE PREFERRED EMBODIMENT

Figure 1:
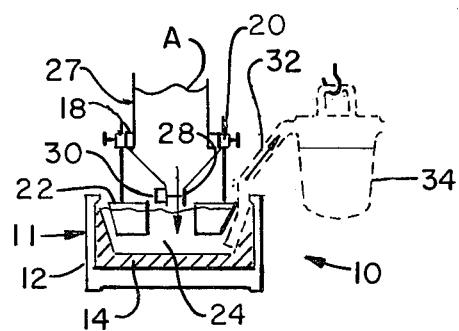
FIG. 1 is an elevational sectional view of a typical electrolysis cell used in the smelting of aluminum according to the Hall process.
Figure 2:
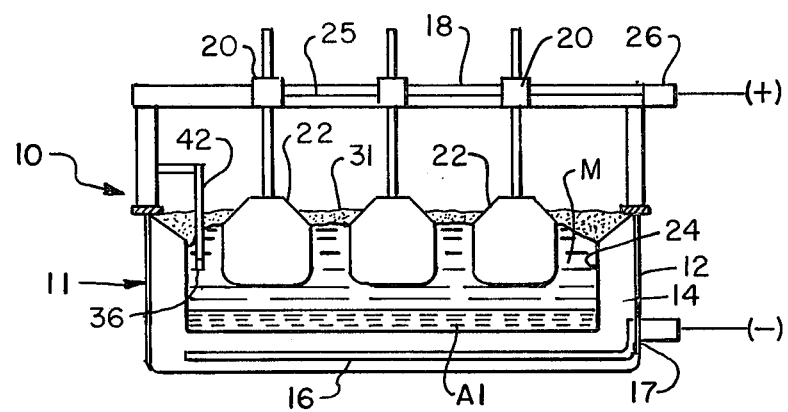
FIG. 2 is an elevational sectional view of the electrolysis cell of FIG. 1, as seen from the side thereof.

A typical electrolysis cell 10 is illustrated in cross section in FIGS. 1 and 2. The cell 10 comprises an open-top vessel 11 formed with a steel structural wall 12 and a carbon refractory liner 14. A collector plate or cathode bar 16, within the carbon liner 14 adjacent but insulated form the lower vessel wall 12, is connected to an exterior electrical connector 17. The connector 17 in turn is adapted to be connected via conventional power leads to the ground or negative terminal($-$) of an electrical DC power supply. A frame member 18 located over the top of the vessel 11 holds brackets 20 each of which in turn supports a carbon anode 22 in a manner that it can be adjusted vertically. The anodes 22 thus can be raised or lowered to varying depths within the vessel opening 24; and are connected via a conductor 25 to a common exterior electrical connector 26. The connector 26 is adapted to be connected via conventional power leads and switching means (not shown) to the positive (+) of the electrical DC power supply. A hopper 27 having an outlet chute 28 located vertically above the vessel opening 24 is designed to hold granular alumina A, which can then be discharged upon opening of valve 30 at the chute 28.

In the normal smelting operation according to the Hall process, the cell 10 is designed to operate with a molten electrolyte at a temperature typically in the range of 950°–1000° C. The electrolyte material are initially added in powdered or granular form to the cell cavity around the anodes 22, consisting in the main of the binary mixture of cryolite ($Na_3AlF_6$) and alumina ($Al_2O_3$), although traces of fluorospar ($CaF_2$) are also generally present. Electric resistance heaters (not shown) can be used to heat the vessel, while also the anodes 22 can be lowered into contact with the carbon liner 14 and a DC electric current passed through the then short circuited anodes 22 and liner 14 to heat the granular composition until it becomes the molten electrolyte. The anodes 22 are then vertically adjusted upwardly to the normal operating position with a small gap (3–10 cms) between the anodes 20 and the carbonized liner 14.

During the typical electrolysis smelting cycle that follows, a DC potential generally between 4 and 6 volts is applied across the carbon anodes 22 and the carbon liner cathode 14, generating approximately 600–800 milliamps of current per $cm^2$ at the anodes 22. The alumina ($Al_2O_3$) breaks down to produce molten aluminum (Al) which being heavier than the molten electrolyte sinks to the bottom of the vessel; while oxygen ($O_2$) goes to the anodes 22 and it combines with the carbon to generate mostly carbon dioxide ($CO_2$) and some carbon monoxide (CO).

Generally current regulating apparatus (not shown) attempts to maintain this current density constant. The anodes are gradually consumed so that the gap above the rising molten aluminum at the bottom of the cell generally will remain quite constant, although the height of the anodes can be periodically adjusted responsive to the current density as a form of the control.

The normal starting alumina concentration by weight in the molten electrolyte mixture is between 6 and 7%; and this concentration is slowly reduced over the initial phase of the smelting cycle lasting generally in excess of 10–12 hours to between approximately 2.2% and 0.5%. Below this range of alumina concentration, the adverse "anode effect" phase of the cycle begins and occurs.

During smelting, the surface of the electrolyte cools sufficiently to crust over as indicated in FIG. 2 at 31. To recharge the cell with alumina when the alumina concentration becomes too low, this crust 31 must be broken and the additional alumina A discharged into the vessel through the hopper chute 28 in sufficient quantities to bring the alumina concentration back up to the approximate starting range of 6–7 wt.%. After perhaps several batches of alumina have been smelted, the molten aluminum metal Al is siphoned off from the bottom of the cell through the tube 32 into ladle 34 (each shown in phantom), and can then be poured into molds (not shown) for casting ingots or the like.

This invention provides for the accurate detection of the sonic resonant frequency of the electrolyte which, when correlated against a prior known data base, gives an accurate indication of the alumina concentration in the electrolyte. The invention utilizes a sonic resonator 36 (see FIGS. 2 and 3) having a continuous tubular side wall 38 closed at one end by wall 40. A transducer 46 is operatively located on the closed wall 40 of the resonator. The resonator 36 is mounted in the molten electrolyte by means of a standard or other support 42, and control leads (not shown) typically are carried in a sheathed cable up the standard 42 between the transducer and an exterior control.

The resonator can be at almost any orientation with the open end 44 directed upwardly, downwardly, horizontally or at an angle anywhere in between. The resonator is however preferably located at an elevation only several centimeters (4–10 cms) above the highest expected level of metallic aluminum during the smelting operation. This provides that a reasonably uniform electrolyte is seen at the resonator, and it is actively participating in the electrolysis process and is therefore near the quasi-equilibrium electrolysis temperature.

As the temperature of the electrolyte will generally be 950° C. or higher, care must be taken to use suitable materials for the resonator and the transducer. In this regard the resonator is preferably fabricated of titanium diboride ($TiB_2$); while the transducer is preferably formed of lithium niobate ($LiNbO_3$) or strontium pyraniobate ($Sr_2Nb_2O_7$)—each of the latter two materials having a Curie point in excess of 1200° C.

Figure 3:
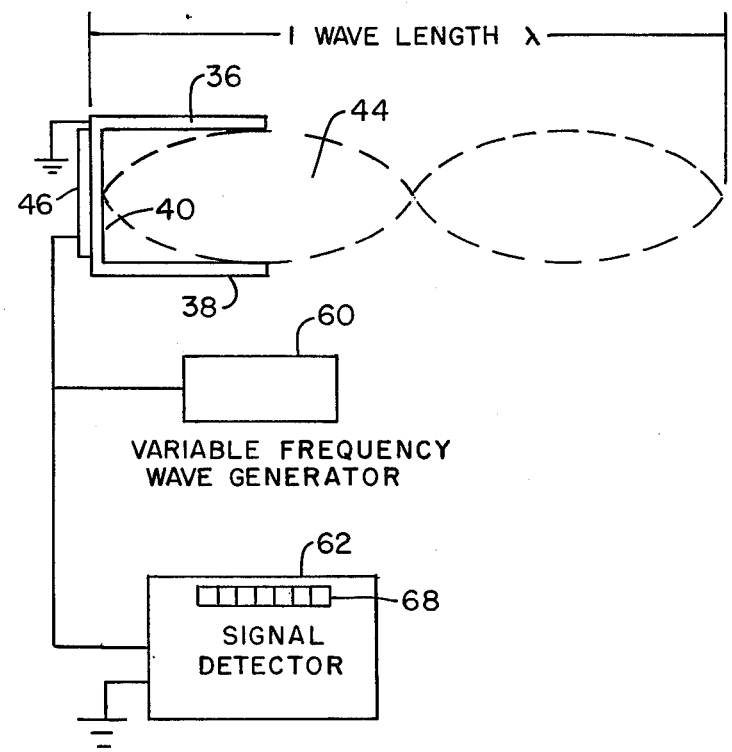
FIG. 3 is a sectional view of the sonic resonator used in the subject invention, as well as a schematic control therefor.

The control circuitry for the resonator is illustrated schematically in block diagram in FIG. 3 and includes the resonator transducer 46 connected by means of a coaxial grounded sheathed cable (not shown) to an adjustable frequency wave generator 60. The generator 60 would effectively be operated in a range of frequencies below 1 MHz. The excited transducer resonator would transmit sonic pulses into the electrolyte, which would be reverberated and dampened by the electrolyte in the resonator, and detected again at sufficiently high quality of resonance by the same transducer. A detector 62 is also connected in circuit with the wave generator 60 so as to detect both the output strength of the sonic signal and its frequency.

The sonic velocity in a liquid equals the wavelength of the impulse multiplied by the exciting frequency of the impulse. The sonic velocity in molten mixtures of this type at approximately 950°–1000° C. is in the range of $1-4 \times 10^5$ centimeters per second; so that at an exciting frequency of approximately 100 kilo Hertz ($10^5$ Hz), the impulse wavelength is in the range of 1–4 centimeters. The sonic resonator 36 is made very precise with the side wall 38 near ¼ this wavelength, or of the order ¼ to 1 centimeter in length. It thus would be what is commonly known as a quarter-wave resonator, and a wave pattern generated upon resonant excitation of the resonator is illustrated with phantom lines 52 in FIG. 3, where the acoustical mismatch occurs at the open end of the resonator.

Figure 6:
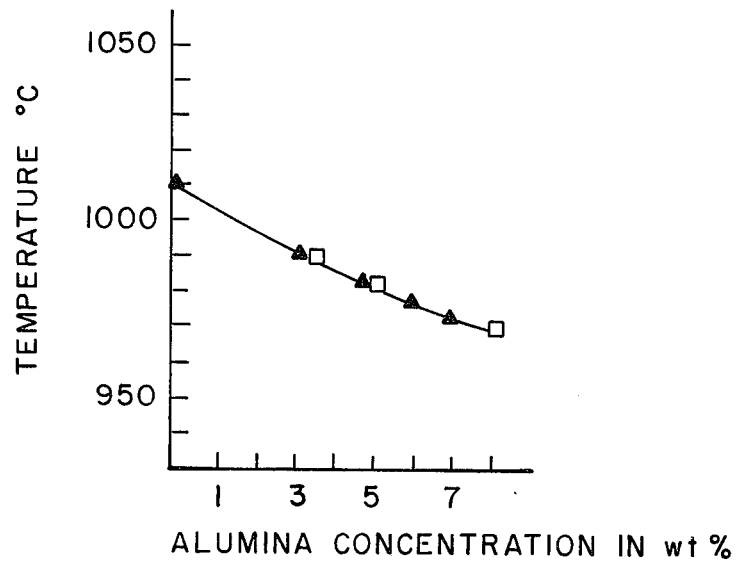
FIG. 6 is a phase diagram of the binary system of cryolite and alumina indicating the phase temperature as a function of alumina by wt.%.
Figure 7:
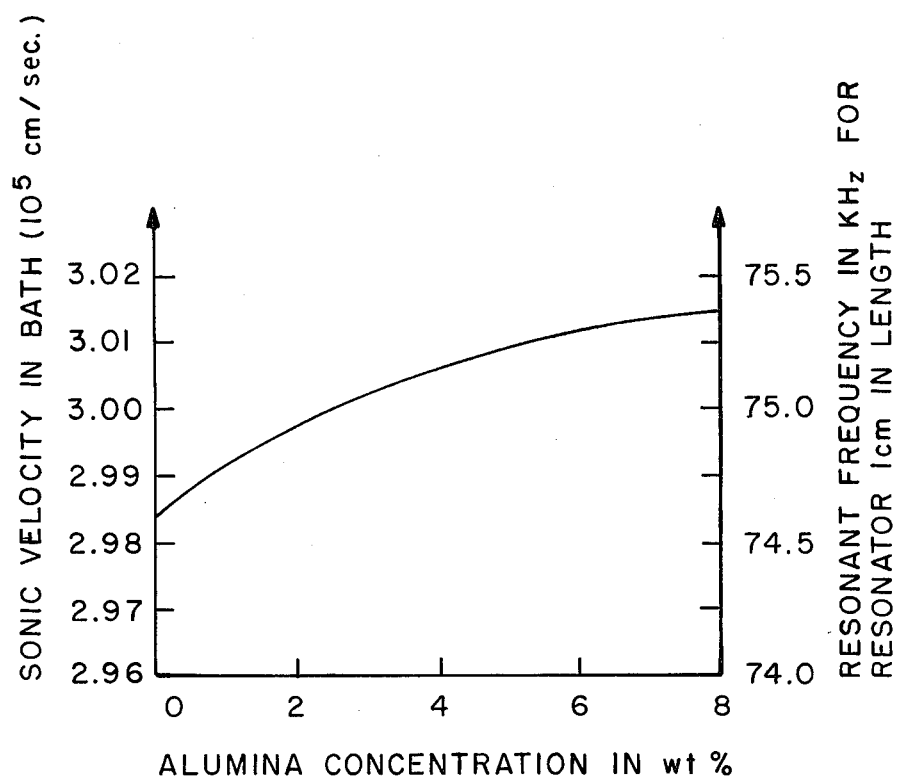
FIG. 7 is a representative curve of a data base that may be established correlating the sonic velocity and resonant frequency relative to the alumina concentration of the electrolyte.

The sonic velocity varies as the mixture density in the bath varies, and increases or decreases as the alumina concentration in the bath increases or decreases. A data base can be established to correlate the natural frequency of the resonator 36 against alumina concentrations in the electrolyte at electrolysis temperatures, and a typical curve is shown in FIG. 7. As illustrated in FIG. 6, the phase diagram of the binary system of cryolite and alumina ($Na_3AlF_6$—$Al_2O_3$) traces a single curve so that for a specific alumina concentration, an equilibrium temperature exists for the electrolyte. This means that when the alumina concentration is measured, the temperature of the electrolyte can also be inferred.

Figure 4:
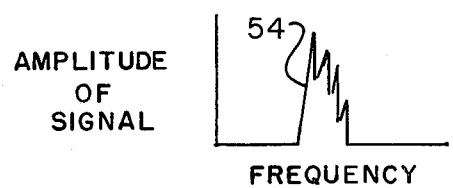
FIG. 4 is a schematic illustration of the sonic signal detected at and near the resonant frequency condition.
Figure 5:
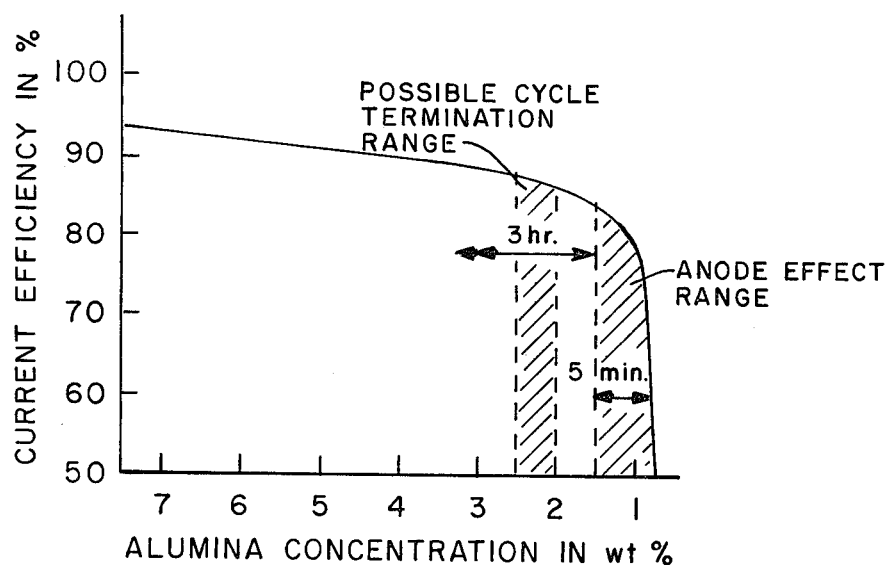
FIG. 5 is a representative curve indicating the current efficiency during electrolysis of the electrolyte as a function of the alumina concentration therein.

A further interesting phenomena relates to the generation and detection of sonic energy in the molten electrolyte with the same resonator, particularly considering sonic absorption. The resonator, excited by a range of frequencies including the resonator frequency, will send out signals that during all frequencies generated by the wave generator 60 except the resonant frequency, will be highly dampened so that the detected energy levels of these signals would be low. At the resonant frequency, however, the detected signal would form a detectable peak as illustrated at 54 in FIG. 4. This detected signal peak 54 would occur only at the resonant frequency, or where the sonic wavelength was four times the length of the quarter wave sonic resonator 38.

The sonic resonator 38 would be calibrated prior to its use in the smelting cell 10 by determining the particular signal frequency needed to produce resonance for different but known wt.% alumina concentrations, that is at 7%, at 6%, at 5%, etc. clear on down to and into the critical low range of perhaps 0.5%, where the anode effect phase of the cycle would exist. In terms of actual use, the data base could be inputed into a ROM or read only memory chip, or a microprocessor (neither being shown).

The instantaneously detected resonant frequency would be compared against this data base in a two variable array, to determine the actual or instantaneous alumina concentration in the electrolyte. With this known data base and comparative technique, the alumina concentration can be determined with good accuracy, at least equivalent to within ±0.10%, for any phase of the smelting cycle. In point of control, the detector device 62 can be used to give the alumina concentration as a direct digital output, as at display 68.

To improve the Hall smelting cycle, the particular control would be set to signal when the alumina concentration reached some predetermined low level still higher than the critical low level where the anode effect phase of the cycle normally would start. As noted, the anode effect typically might start in the high range of approximately 2.2 wt.% alumina concentration, but might also start at some ranges even as low as 0.5%. In order to provide some margin for safety, it would be preferred to seek some higher alumina concentration, perhaps between 2.7–2.5 wt.%. The detected low alumina concentration in the electrolyte would cause a signal that could trigger automatic means (not shown) for breaking the crust 31 and then adding the alumina from the discharge chute 28 by opening valve 30, or that merely would alert an operator who then would manually add additional alumina.

The subject control can thus accurately and consistently provide that the alumina concentration is recharged before it reaches the low critical level, and that the smelting cycle is operated only in the efficient ranges and not in the anode effect range. This consequently would stabilize the input power applied between the anodes and cathode as well as further would minimize cell overheating and chemical waste.

While the particular invention has been disclosed with specific reference to the smelting of aluminum, other smelting operations could be advantageously controlled. Also, detection and/or control can be made of other high temperature processes involving a molten liquid, particularly where the parameter of interest is functionally related to the sonic velocity. Accordingly, it is intended that the invention be limited only by the claims hereinafter following.

The embodiments of the invention in which an exclusive property or privilege is claimed are defined as follows:

1. For use in smelting aluminum by electrolysis of a molten electrolyte at temperatures between 950° and 1000° C., where alumina would normally start at 6–7 wt.% concentration of the electrolyte and decline to 2.2–0.5 wt.% concentration near the end of the cycle where an anode effect would begin, a control for accurately determining when a predetermined alumina concentration of the order of 2.7–2.5 wt.% is reached to provide for recharging the electrolyte with alumina before any anode effort might begin, comprising a sonic resonator submerged in the electrolyte, a transducer coupled to the resonator, a wave generator for exciting the transducer and resonator throughout a range of frequencies through and including the resonant frequency of the resonator in the electrolyte, means for detecting the sonic signal from the excited resonator and particularly for isolating the resonant frequency, and means including a data base for correlating the resonant frequency and the alumina concentration throughout the range of alumina concentrations encountered in the smelting cycle, whereby periodic repeated findings of the resonant frequency effectively can provide the instantaneous alumina concentrations during the smelting cycle and specifically can identify when said alumina concentration reaches said predetermined alumina concentration.

2. A control combination according to claim 1, wherein the transducer is formed of lithium niobate ($LiNbO_3$).

3. A control combination according to claim 1, wherein the transducer is formed of strontium pyroniobate ($Sr_2Nb_2O_7$).

4. A control combination according to claim 1, wherein the resonator is formed of titanium diboride ($TiB_2$).

5. A control combination according to claim 1, wherein the resonator is formed as a tube having one closed end and having cylindrical side walls formed precisely at $\frac{1}{4}$ the length of an anticipated wavelength of a sonic impulse through the electrolyte excited at an approximately known frequency.

6. A control combination according to claim 3, wherein the resonator is formed with the cylindrical side walls on the order of $\frac{1}{4}$-1 centimeter length, and wherein an exciting frequency in the range of 100 KHz will produce an anticipated resonant condition of the resonator in the electrolyte for the alumina concentration in the range between 7 and 0.5 wt.%.

7. In the smelting of aluminum by electrolysis of a molten electrolyte at temperatures between 950° and 1000° C., where alumina would normally start at 6–7 wt.% concentration of the electrolyte and decline to 2.2–0.5 wt.% concentration near the end of the cycle where an anode effect would begin, a method for accurately determining when a predetermined alumina concentration of the order of 2.7–2.5 wt.% is reached to provide for recharging the electrolyte with alumina before any anode effort might actually begin, comprising the steps of submerging a sonic resonator in the electrolyte at a representative level thereof, periodically exciting the resonator throughout a range of frequencies through and including the resonant frequency of the resonator in the electrolyte, detecting for each excitation of the resonator the instantaneous resonant frequency thereof, correlating this against a data base calibration of the resonator at known alumina concentration throughout the smelting cycle, whereby the instantaneous resonant frequency effectively can provide the instantaneous alumina concentrations during the smelting cycle so as to allow the identification thereof when said alumina concentration reaches said predetermined alumina concentration.

8. A control for determining the relative wt.% concentration in a specific range of interest of one component in a multiple component molten liquid mixture, comprising a quarter-wave sonic resonator submerged in the liquid mixture, a transducer coupled to the resonator, a wave generator for exciting the transducer and resonator throughout a range of frequencies through and including the resonant frequency of the resonator in the liquid mixture, means for detecting the sonic signal from the excited resonator and particularly for isolating the resonant frequency, and means for comparing this resonant frequency in a data base correlating the resonant frequency and the component concentration throughout said specific range of interest operable thereby to provide the instantaneous relative wt.% concentration of the component in the mixture.

* * * * *